United States Patent [19]

Stephenson

[11] Patent Number: 5,801,061

[45] Date of Patent: Sep. 1, 1998

[54] METHOD FOR THE COLORIMETRIC DETERMINATION OF ANALYTES IN THE PRESENCE OF INTERFERING PARTICULATE MATERIALS

[75] Inventor: Harry Thomas Stephenson, Elkhart, Ind.

[73] Assignee: Environmental Test Systems, Inc., Elkhart, Ind.

[21] Appl. No.: 839,220

[22] Filed: Apr. 22, 1997

[51] Int. Cl.$^6$ .................................. G01N 33/24
[52] U.S. Cl. .................. 436/169; 436/28; 422/56; 422/61
[58] Field of Search .................. 422/57, 58, 56, 422/61; 436/169–170, 25, 28

[56] References Cited

U.S. PATENT DOCUMENTS

| | | | |
|---|---|---|---|
| 3,552,925 | 1/1971 | Fetter | 422/56 |
| 4,126,417 | 11/1978 | Ewards | 422/56 |
| 5,166,051 | 11/1992 | Killeen et al. | 422/57 |
| 5,470,752 | 11/1995 | Burd et al. | 422/56 |
| 5,500,375 | 3/1996 | Lee-Own et al. | 422/57 |

*Primary Examiner*—Lyle A. Alexander
*Attorney, Agent, or Firm*—Zarley, McKee, Thomte, Voorhees, & Sease

[57] ABSTRACT

The present invention involves a unitized dry reagent test device and method for removing the interference caused by suspended particulate materials in the calorimetric determination of analytes in samples containing such materials. More specifically, the testing methodologies of the present invention comprise the use of a multilayer reagent impregnated matrix having known particulate removal characteristics attached to a test fluid impervious support means which has known light transmission characteristics. On-site or field testing of soil samples is an advantageous and representative application of the devices and methods of the present invention.

8 Claims, 1 Drawing Sheet

5,801,061

METHOD FOR THE COLORIMETRIC DETERMINATION OF ANALYTES IN THE PRESENCE OF INTERFERING PARTICULATE MATERIALS

FIELD OF THE INVENTION

The present invention relates to a unitized dry reagent test device and method for the calorimetric determination of analytes in samples containing interfering particulate materials such as in the chemical analysis of soil samples. Although the methods and devices of the present invention are ideally suited for field or on-site testing, they can also advantageously be used in the laboratory for screening and facilitating the testing of multiple samples.

BACKGROUND OF THE INVENTION

Numerous commercial analytical chemistry procedures involving solid organic and inorganic samples require a multiplicity of steps to complete. Of the many steps, probably the one presenting the most problems and adding the most variables to the analysis, is the extraction procedure which requires that the solid sample be intimately mixed with an extracting fluid to solubilize the analyte or chemical parameter of interest. The second most troublesome step involves the separation of the solubilized analyte or chemical parameter in the extracting fluid from the extraneous and/or the particulate materials in the sample which may cause interference with the ensuing calorimetric or spectrophotometric procedures being employed. This separation procedure usually involves passing the liquid sample mixture through a filter element or paper or centrifuging the sample to separate the clear supernatant from the interfering materials and decanting the clear fluid off for the actual analysis. Obviously these steps are difficult and time consuming to perform in the field. Analytical extraction and separation procedures involving soil samples are particularly difficult and slow and usually present serious procedural problems.

More specifically, the procedures used in the chemical analysis of soil samples usually involve the following steps: collecting representative samples of soil; measuring a predetermined volume or weight of soil; solubilizing the analytes or parameters of interest from the sample into an aqueous extracting fluid; filtering the fluid to remove the extraneous particulate materials and finally performing the analysis for the analyte of interest.

The more usual methods for determining the analytes of interest in soil and other sample materials involve calorimetric procedures which in themselves are commonly several step procedures. Colorimetric procedures involve contacting the analyte with a reagent or reagent composition which changes from one color to another or changes in color intensity depending on the amount of analyte present in the solution or sample being tested.

It will be appreciated that when numerous samples are tested for analytes or chemical parameters such as pH, either in the field (on-site) or in the laboratory, any elimination or simplification of a step or steps in the procedure is very advantageous in that it translates into a significant savings of time, materials and cost to the analyst as well as the person interested in the test result.

DESCRIPTION OF THE PRIOR ART

Reagent strips which perhaps are better known as "dip and read" test devices first appeared in the last century with the introduction of the so-called litmus papers. These simple test devices were first used to test fluids for pH or at least the presence of acidic or basic components in liquid systems. Since then, the scientific and patent literature is replete with references to these test devices which have grown in complexity and sophistication and extend into all types of testing, from medical to industrial to recreational applications.

Perhaps the first patent references referring to reagent strips appeared in the sixties and related to medical test devices. At first these test devices were elongated strips of absorbent paper, one end or all of which was impregnated with a solution of a chemical test composition and then dried to allow the device to be mass produced and later used as an individual test device. Later, when multiple reagent areas appeared on a single test strip, a semi-rigid plastic strip replaced the paper strip and small square areas of individual reagent pads were simply glued or affixed to the plastic "handle". Reagent strip appearance and construction remain essentially the same to the present time.

Traditional use of reagent strips calls for the analyst to immerse the reagent area into the fluid being tested, remove the same from the fluid and after a prescribed period of time or in some instances immediately, comparing the color of the appropriate reagent pad to a precalibrated color chart to obtain an actual value or analytical result. Almost universally the calorimetric reaction of the test device is read by observing the color of the top surface of the reagent matrix pad and comparing that upper pad surface color to the color chart. There are, however, some exceptions:

U.S. Pat. No. 3,552,925 to Fetter (1971) discloses and claims a multilayer device for removing red blood cells from whole blood to allow the detection of analytes in the blood using a reagent strip type device containing certain salts. FIG. 3 shows a device wherein the color reaction is read on the reverse side of the support means. See also column 4, lines 29–31. As noted in the specification, the mechanism of the reaction is unknown and the procedure is not always effective in removing such coloration from the blood sample. Moreover, it should also be noted that it is the salt and not the matrix that appears to remove the red coloration from the whole blood.

U.S. Pat. No. 5,470,752 to Burd et al. (1995) discloses and claims a multilayer test device for the determination of fructosamine in which the calorimetric result using a reagent strip like device is read on the reverse or bottom side thereof. See FIGS. 1B to 4B. There is however a significant difference between this device and the concept of the present invention in that the Burd et al. device is not a true "dip and read" type test implement. The sample is applied to the top, flipped over and read through an aperture on the bottom, whereas the present device is actually dipped into the fluid being tested and read through a specially designed support means.

SUMMARY OF THE INVENTION

The present invention involves the use of a dry reagent test composition incorporated into or onto a matrix having known porosity and filtering characteristics and attaching the matrix to a fluid impervious support means for the matrix in such a way that any interfering particulate substances contained in the fluid being tested, are removed from the area of the matrix being read. In its simplest configuration, the matrix comprises a reasonably sized square of absorbent filter type paper or other absorbent material having known filtering characteristics which has been impregnated with a test reagent composition which is specifically reactable with the analyte being detected to give a calorimetric response, the paper square being attached by adhesive to one end of a longer strip of semirigid fluid impervious plastic having defined or known light or color transmission characteristics.

In use, the reagent strip test devices of the present invention are dipped into the fluid being tested which contains interfering particulate materials, the fluid enters into and penetrates the absorbent matrix which removes the particulate materials, the clear fluid containing the analyte migrates through the matrix reacting with the test reagent and the color developed is read on the matrix through the support means which has known and well defined light and color transmission characteristics. Obviously, such a simple configuration can be modified significantly to achieve advantageous combination particulate matter removal/color response objectives depending on the light and color characteristics of the support means as well as the matrix materials used as will be described hereinafter.

BRIEF DESCRIPTION DRAWINGS

DESCRIPTION OF THE PREFERRED EMBODIMENTS

Figure 1:
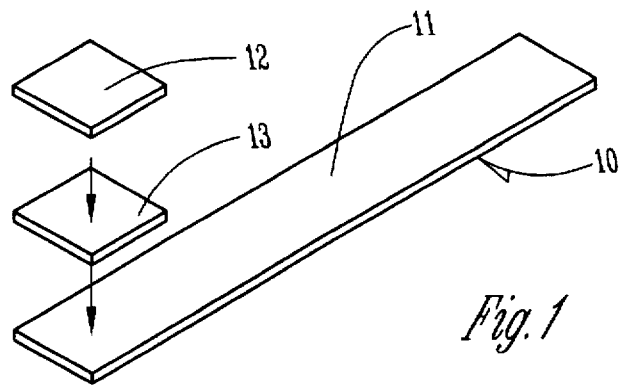
FIG. 1 shows an exploded perspective view of a simple reagent strip test device comprising a matrix and a plastic handle.

The test devices of the present invention basically comprise at least a two component multilayer structure. The first layer comprises a matrix consisting usually of an opaque porous material into or onto which a test reagent composition is incorporated. The test reagent composition will be described more fully hereinafter. The function of the matrix is to 1. hold the test reagent composition in place to contact the analyte in the fluid being tested and 2. remove, by filtration or other means, any interfering fluid insoluble particulate matter contained in the sample fluid. Accordingly, the matrix must be an opaque material having well defined, known filtration or porosity characteristics depending on the size and/or chemical characteristics of the interfering particulate materials contained in the test fluid sample. Preferably the matrix is a flat absorbent paper or paper-like material which commonly is used as a filter material. Other materials such as membranes, sintered glass, glass fibers, flocculants, diatomaceous earth, activated carbon and so forth may be used. The matrix layer may also itself be a multilayer structure so long as it serves to perform the functions described above.

Since the matrix serves as the mechanism for removing interfering materials and substances from the fluid being tested, the porosity and filtering capacity and mechanism of filtration of the matrix must be known and selected for the specific application. For example, if the sample being tested is related to soil testing and the suspended material interfering with the calorimetric analysis is finely suspended clay, the matrix material must have a porosity of sufficient smallness to remove such fine particles. On the other hand, if the pores of the matrix are too small the time involved in allowing the test fluid to penetrate the matrix will be too long for a practical and useful test device. Moreover, if the mechanism of particulate material removal is adsorption as opposed to simple filtration, then the known particulate removal characteristics of the matrix must be defined in terms of adsorption function and capacity. As used herein, the term filtering includes both the physical removal of particulate materials as determined by the pore size of the filter material and by chemical removal as by adsorption or absorption by matrix material itself.

More specifically, when the sample being tested is soil or a similar solid particulate sample material, the matrix should have the capability of removing interfering particulate materials having a diameter of from about 1 micron (0.0001 mm) and larger to about 200 microns (0.02 mm) and larger in size. By this it is meant that depending on the application, the matrix selected should be capable of removing mixes of interfering particles from the extracted test sample of from about 1 micron and up to about 200 microns and up. Accordingly the matrix should have a pore size of about from 1 micron to 200 microns and preferably about from 2 microns to 20 microns.

The second layer comprises basically a support means for holding the matrix and forcing the test fluid sample to flow through the matrix and test reagent composition. The support means also performs the important function of allowing the reading of the color reaction of the test composition with the analyte after the matrix eliminates the interference due to any particulate insoluble materials in the test fluid. As a practical matter, the matrix is attached to the support means by using an adhesive material or layer between the matrix and support means. In its more usual configuration, the matrix and support means are flat materials and are intimately attached to each other by means of a layer of double faced clear tape as will be described more fully hereinafter.

The support means consists of a clear or translucent substance, usually plastic, having defined or known optical or light transmitting characteristics depending upon the color of the test reaction and the desired final color of the light being visually read by the analyst or being read by an instrumental means used by the analyst. For example, if the sample contains interfering soluble colored materials in addition to particulate insoluble materials, the support means may comprise a colored filter material which in effect allows the reading of a color reaction by changing the final color of the light being transmitted to the analyst. More usually, the support means is a clear material having neutral density filter characteristics.

Figure 2A:
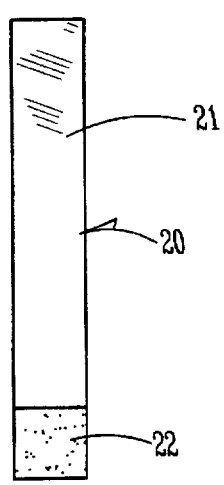
FIG. 2A, 2B and 2C show front, back and side views respectively of the reagent strip test device shown in FIG. 1, 2C depicting the flow of test fluid and the reading side of the test device.
Figure 2B:
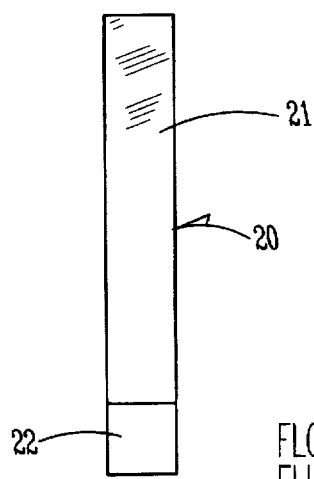
Figure 2C:
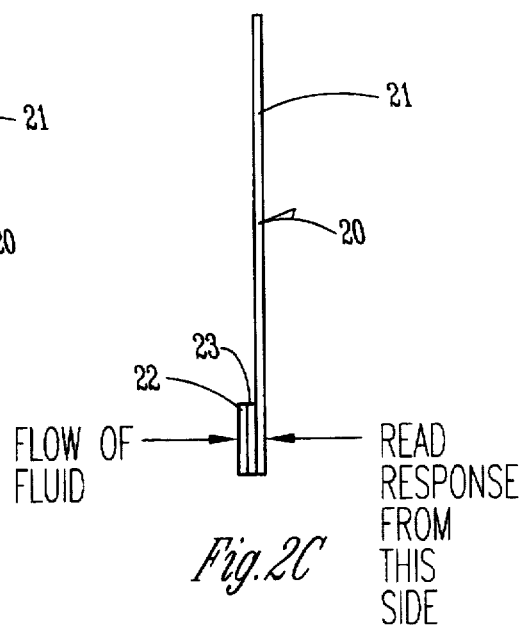

Referring now to the drawings, the structure of a simple test device of the present invention is shown in FIG. 1. This figure represents an exploded perspective view of a reagent strip device 10 consisting of an elongated plastic handle 11 which forms the support means to which is attached at the end thereof, using a double faced clear plastic adhesive tape 13, an absorbent matrix 12 which incorporates the test reagent composition. FIGS. 2A, 2B, and 2C show front, back and side views of the same type of reagent strip test device as shown in FIG. 1, wherein the support means 21 consists of a clear test fluid impervious plastic material to which the matrix 22 is attached thereto at one end thereof by means of a clear double faced adhesive tape layer 23 as shown in FIG. 2C. The double faced adhesive tape forms an intimate attachment area between the support means 21 and the matrix 22 resulting in a test device having a front (matrix) side and a back (support means) side.

The resulting test device comprises a first layer matrix material intimately attached to a second layer support means, the two layers being in juxtaposition with each other forming a common reading area therebetween, when viewed through the support layer.

In use, the test device 21 is dipped into the test sample containing fluid insoluble particulate interfering substances, the fluid enters the matrix from the front side as shown in FIG. 2C, the particulate material removed and the clear fluid reacts with the test reagent to form a color depending on the amount of analyte present in the fluid and the color read on the reverse or rear side of the device as depicted in FIG. 2C.

Finally, it should be noted that the attachment material and means must also be considered when designing the devices of the present invention since the color response is read on the surface of the matrix through both the support means and the attachment layer. Because of this, such attachment material must have at least neutral filter density light transmission characteristics.

The test compositions of the present invention may be any of various chemical mixtures which react specifically with certain analytes found in test samples of interest to give a colorimetric (color forming) reaction which depends on the amount of analyte found in the test sample. This color reaction may then be read using visual means such as by comparing the color to a precalibrated color chart or using an instrumental means which measures the amount of color formed and optionally interprets the relationship of color developed to concentration of analyte. As used herein, the term color response means either a change in color or an increase in the intensity of a particular color. When using an instrumental readout means, the term color response may also include a change in the portion of the electromagnetic spectrum beyond or below the visual range.

What is claimed is:

1. A method for the determination of the concentration of an unknown analyte in a solid soil sample containing interfering water insoluble particulate materials, said method comprising:

a. mixing the solid soil sample with an aqueous extracting fluid to generate an extracted liquid test solution of the unknown analytes mixed with a dispersion of the water insoluble particulate material from the solid soil sample;

b. contacting the liquid test solution with a test device comprising an opaque matrix having filtering characteristics capable of removing the interfering water insoluble particulate materials, the matrix incorporated with the dried residue of a test composition reactable with the analyte to give a detectable response thereto in proportion to the amount of analyte present in the liquid test solution, the matrix being attached to a test fluid impervious support means having known light transmission characteristics forming a continuous face to face attachment area between the matrix and the support means, resulting in a device having a matrix side and a support means side; and, c. reading and estimating the degree of detectable response of the test composition in the matrix through the attachment area on the support means side and correlating such response to that obtained using the same test devices with a series of standard concentrations of analyte in aqueous solutions to allow estimation of the concentration of unknown analyte in the test fluid.

2. A method as in claim 1 wherein the matrix has a pore size of about from 1 micron to 200 microns.

3. A method as in claim 1 wherein the matrix has a pore size of about from 2 microns to 20 microns.

4. A method as in claim 1 wherein the matrix is a flat absorbent filter paper.

5. A method as in claim 1 wherein the support means is a clear plastic material having neutral filter density characteristics.

6. A method as in claim 1 wherein the support means is an elongated rectangular plastic material and the matrix is attached to one end thereof.

7. A method as in claim 1 wherein the matrix is attached to the support means using a plastic double sided adhesive material.

8. A method as in claim 7 wherein the plastic double sided adhesive material has neutral filter density characteristics.

* * * * *